(12) United States Patent
Yanagiuchi et al.

(10) Patent No.: US 7,091,484 B2
(45) Date of Patent: Aug. 15, 2006

(54) METHOD AND APPARATUS FOR CRYSTAL ANALYSIS

(75) Inventors: Katsuaki Yanagiuchi, Tokyo (JP); Wakako Okawa, Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 10/988,086

(22) Filed: Nov. 12, 2004

(65) Prior Publication Data

US 2005/0103995 A1 May 19, 2005

(30) Foreign Application Priority Data

Nov. 14, 2003 (JP) ............................. 2003-385678

(51) Int. Cl.
*H01J 37/252* (2006.01)
*H01J 49/46* (2006.01)
*G01N 23/207* (2006.01)
*G01N 23/225* (2006.01)

(52) U.S. Cl. ............... 250/309; 250/306; 250/307; 250/492.3; 250/491.1; 250/492.1; 250/492.2; 250/492.21

(58) Field of Classification Search ............... 250/309, 250/306, 307, 492.1, 492.2, 492.21, 492.3, 250/396 R, 397, 398, 399, 396 ML
See application file for complete search history.

(56) References Cited

U.S. PATENT DOCUMENTS 4,233,509 A * 11/1980 Tamura et al. ............ 250/306
5,023,453 A * 6/1991 Adachi et al. ............ 250/309
5,089,699 A * 2/1992 Ose et al. ............... 250/306
6,664,552 B1 * 12/2003 Shichi et al. .......... 250/492.21
6,794,663 B1 * 9/2004 Shichi et al. .......... 250/492.21
2004/0206903 A1 * 10/2004 Ushiki et al. ............ 250/306
2005/0103995 A1 * 5/2005 Yanagiuchi et al. ....... 250/309

FOREIGN PATENT DOCUMENTS

| JP | 403289551 A | * 12/1991 |
| JP | 5-264477 | 10/1993 |
| JP | 8-287612 | 11/1996 |
| JP | 2003-021609 | 1/2003 |

* cited by examiner

*Primary Examiner*—John R. Lee
*Assistant Examiner*—Bernard E. Souw
(74) *Attorney, Agent, or Firm*—Katten Muchin Rosenman LLP

(57) ABSTRACT

The method of measuring crystallographic orientations, crystal systems or the like of the surface of a specimen has steps of: irradiating the specimen with an ion beam; measuring the secondary electrons generated by the irradiation of the ion beam; repeating the irradiation of the ion beam and the measurement of the secondary electrons with each variation in an angle of incidence of the ion beam with respect to the specimen; and determining the crystalline state based on the variation in the amount of the secondary electrons corresponding to the variation of the angle of incidence.

4 Claims, 3 Drawing Sheets

METHOD AND APPARATUS FOR CRYSTAL ANALYSIS

BACKGROUND OF THE INVENTION

1. Field of the Invention

The present invention relates to a method of crystal analysis and an apparatus for crystal analysis capable of analyzing crystalline states such as the crystallographic orientations of individual crystal grains on the surface of a specimen.

2. Description of the Related Arts

The recent development of micromachining technologies has come to require the technologies for analyzing crystal system and crystallographic orientations of crystal grains on a solid surface or the like. For example, a fine copper (Cu) wiring formed by a plating process has been employed for a coil wiring of a write element for a magnetic head employed in a hard-disk drive. In this copper wiring, the orientations of microcrystals and the structures of crystal-grain boundaries make a difference in a resistance value of the wire, causing variations in the characteristics of the magnetic head. For this reason, control of crystal growth has become one of the requirements for fabricating a magnetic head of high reliability and thus grasping of diameters of microcrystal grains, states of grain boundaries and crystallographic orientations has become of great interest.

Concerning the diameters of crystal grains and states of grain boundaries, it is easy to obtain knowledge through observations by an electron microscope and observations by a scanning ion microscope (SIM). As a practical method available for obtaining the knowledge specifically on the crystallographic orientations of the copper crystal grains that make up the copper wiring described above, however, there has been known only the EBSP (Electron BackScattering Pattern method or the Electron BackScattering diffraction Pattern) method. In the EBSP method, an electron beam impinges on a specimen at a large incidence angle in a scanning electron microscope (SEM); the electron beam experiences reflections and diffraction in the specimen; and is scattered backwards to form a diffraction image. This diffraction image (i.e., diffraction pattern) varies in its bandwidth and intensity depending on the crystalline structure at the incident position of the electron beam. Accordingly, the crystal system and the crystallographic orientation can be determined by analyzing the obtained diffraction pattern. Performing the analysis of the pattern while scanning a specimen surface with the electron beam enables obtaining the knowledge on the two-dimensional distribution of the crystallographic orientations on the specimen surface.

However, a problem has been that, because, in the EBSP method, the electron beam impinges on a specimen surface at a large angle of incidence, minute unevennesses of the surface affect on the result of the analysis and the correspondence between the distribution of the crystallographic orientations observed through the EBSP method and the microscopic image observed through the ordinary scanning microscopic photographs cannot easily be identified. Furthermore, because the diffraction pattern is caused by the Bragg reflection from crystal grains, it is basically difficult to have the resolution (ie., spatial resolving power) raised higher than the existing value, practically the resolution being of the order of several tens of nanometers.

An incidence angle described herein stands for the angle measured from the direction of the normal of the plane of incidence.

While a crystal system and a crystallographic orientation can be decided by the X-ray diffraction method as well, it is difficult in the case of the X-ray to narrow the beam and consequently the resolution is of the order of ten micrometers. Furthermore, the penetration depth of the X-ray is so deep that it is difficult to decide the crystallographic orientation in the outermost surface of a specimen. Japanese Patent Laid-open Publication No. H05-264477 (JP, 5-264477A) discloses a method of analyzing crystallographic orientations of the crystal grains in the surface layer of a specimen through the use of a X-ray, in which a collimated X-ray is applied to a specimen at a large angle of incidence, i.e., at a grazing angle along the specimen surface and, based on the obtained diffraction circles, the crystallographic orientations of the microcrystals in the surface layer are measured.

Japanese Patent Laid-open Publication No. 2003-21609 (JP, P2003-21609A) discloses a method of detecting a crystal axis of a specimen using the Rutherford backscattering analyzer of the parallel magnetic field type that has performance of converging the ions back-scattered from the specimen, the surface of which is irradiated with an ion beam, on the beam axis through the use of the magnetic field parallel to the incident ion beam. In this method, the distribution of detected quantity of the scattered ions is obtained making use of the two-dimensional ion detector and the detection of the crystal axis of the specimen is performed on the basis of the obtained distribution. This method, however, is problematic in that the measuring devices to be employed tend to be complicated, such as a two-dimensional ion detector, a parallel magnetic field generator and the like and in addition, a long measurement time tends to be required for measuring the two-dimensional distribution of the scattered ions.

As described above, the EBSP method is widely employed at present as a method of analyzing and identifying the crystal systems and crystallographic orientations of the crystal grains on a specimen surface made up of fine crystal grains. The EBSP method, however, is problematic in that because the electron beam impinges on a specimen surface at a large angle of incidence, minute unevennesses of the surface affect on the result of the analysis, and that the resolution is of the order of tens of nanometers. While alternatively to the EBSP method, there exist methods of analyzing and identifying the crystal systems and crystallographic orientations of fine crystal grains on a specimen surface, such methods are not necessarily practical as compared to the EBSP method.

SUMMARY OF THE INVENTION

It is an object of the present invention to provide a method of crystal analysis capable of measuring the crystallographic orientations and crystal systems of crystal grains on a specimen surface with high resolution and with ease.

It is another object of the present invention to provide an apparatus for crystal analysis capable of measuring the crystallographic orientations and crystal systems of crystal grains on a specimen surface with high resolution and with ease.

The density in an image of a scanning ion microscope represents the amount of the secondary electrons emitted from the surface of a specimen in direct correspondence. The amount of the emitted secondary electrons, however, is significantly decreased in the area where the channeling of the incident ion takes place, because the incident ion can enter the specimen to advance into a deep penetration depth in the area. Thus, it is determined that a dark image portion in an image of the scanning ion microscope represents the area where the ion channeling takes place. While it has been known so for that the image of the scanning ion microscope depends on the ion channeling phenomenon in a specimen, the case has not been known in which images of a scanning ion microscope are acquired at a variety of angles of incidence of an ion beam with respect to a specimen and the variation in the densities of the acquired images is focused on as an object for study.

The present inventors have attained novel knowledge and achieved the present invention, wherein the knowledge is that it is possible to discriminate the crystallographic orientations of the crystal grains on a specimen surface by tracking the variation of density in the image of the scanning ion microscope versus a variation of the incidence angle of the ion beam. The channeling is a phenomenon closely related to atomic alignments in a crystal, and consequently it is feasible to analyze atomic arrangements in a crystal based on the variation of the amount of the secondary electrons depending on an incidence angle of the ion beam, thereby enabling identification of the crystallographic orientations of the crystal grains on the surface of a specimen. In the case where the specimen has different crystal phases in a mixed phase configuration, the crystal phases and the crystal systems to which respective crystal phases belong, of the crystal grains can be identified as well.

The method of crystal analysis according to the present invention is a method of analyzing a crystalline state on a surface of a specimen, comprising the steps of; irradiating the specimen with an ion beam; measuring the secondary electrons generated by irradiation of said ion beam; repeating said irradiating step and said measuring step with each variation in an angle of incidence of the ion beam with respect to the specimen, and determining the crystalline state based on the variation in the amount of the secondary electrons corresponding to the variation of the angle of incidence.

In the present invention, the crystalline state is typically a crystallographic orientation of each of crystal grains present on the surface of the specimen. In addition, the determination of the crystalline state can include identification of the crystal phase and the crystal system to which each crystal grain belongs. The crystallographic orientation is determined, for example, based on the difference between the angle of incidence of the ion beam corresponding to the maximum measured amount of the secondary electrons and the angle of incidence of the ion beam corresponding to the minimum measured amount of the secondary electrons. The method of crystal analysis according to the present invention allows analyzing the crystallographic orientations at a point or in a zone on the surface of a specimen at the same time in easy combination with the scanning ion microscopic observations. In this case, the method comprises the steps of: irradiating the specimen while scanning with a focused ion beam; measuring secondary electrons created by the ion beam irradiation to acquire a scanning ion microscopic image: repeating the irradiating step and the measuring step with each variation in an angle of incidence of the ion beam with respect to the specimen, and determining the crystallographic orientation based on the variation in the densities of a plurality of the scanning ion microscopic images acquired at different angles of incidence.

The crystallographic orientation of a crystal can be decided by calculating a difference between the angle of incidence corresponding to the darkest image of a plurality of the images of the scanning ion microscope and the angle of incidence corresponding to the whitest image for each point or zone on the surface of the specimen, and identifying the crystallographic orientation based on the calculated difference. The difference between an angle of incidence corresponding to the darkest image and an angle of incidence corresponding to the whitest image is herein referred to as a black-white inversion angle. A variety of methods of determining a crystallographic orientation or the like can be envisaged alternatively to the method based on the black-white inversion angle, as can be known from the study on the channeling of ions in a crystal. It is preferred to decide the crystallographic orientations for a plurality of points or zones on the surface of a specimen and represent a distribution of the crystallographic orientations on the surface of the specimen.

The apparatus for crystal analysis according to the present invention is an apparatus for analyzing a crystallographic orientation at each point or in each zone on a surface of a specimen, comprising: an ion optical system that irradiates the surface of the specimen scanning with a focused ion beam; a detector that detects secondary electrons generated by irradiation of the ion beam and provides a detection signal; an image processor that acquires a scanning ion microscopic image based on the detection signal; an angle adjustment unit that varies an angle of the specimen with respect to the focused ion beam; a storage device that stores the scanning ion microscopic images acquired by the image processor; a controller that controls the angle adjustment unit to keep the angle of the specimen fixed while acquiring each scanning ion microscopic image and vary the angle of the specimen with each acquisition of the scanning ion microscopic image; and a crystallographic orientation calculation unit that determines the crystallographic orientation based on a variation in densities of a plurality of the scanning ion microscopic images stored in the storage device.

The present invention observes the amount of the secondary electrons when irradiating the surface of a specimen with an ion beam, follows up the variation in the amount of the second electrons when the angle of incidence of the ion beam with respect to the specimen varies, and identifies the crystallographic orientation and crystal system on the specimen. While the equivalent measurement results can be obtained by means of the EBSP method as well which irradiates with an electron beam, the ion beam irradiation at a small angle of incidence, i.e., in the angular direction nearer the normal line of the surface of the specimen according to the present invention allows easy comparison of the observed microscopic images with the identified results of the crystallographic orientations. Furthermore, in the EBSP method, it is basically difficult to enhance the resolution, because a diffraction beam created by means of the Bragg diffraction is employed. In contrast, because the present invention is based on the channeling phenomenon of ions, which are particles, an improvement of the resolution is easy, and it is enabled to determine the crystallographic orientations of finer crystal grains. While the resolution achieved by the EBSP method is the order of several tens of nanometers, it is enabled according to the present invention easily to obtain the resolution of several nanometers and if the diameter of the focused ion beam is made thinner, further enhancement of the resolution can be attained.

The method according to the present invention has high affinity to a scanning ion microscopic observation, in which microscopic images are produced through secondary electrons by ion-beam-scanning the surface of a specimen, and allows implementing through the use of an existing scanning ion microscope without adding a particular mechanism, provided that only a mechanism for adjusting the orientation of a specimen is provided.

The above and other objects, features, and advantages of the present invention will become apparent from the following description with reference to the accompanying drawings, which illustrate examples of the present invention.

DETAILED DESCRIPTION OF THE PREFERRED EMBODIMENT

Figure 1:
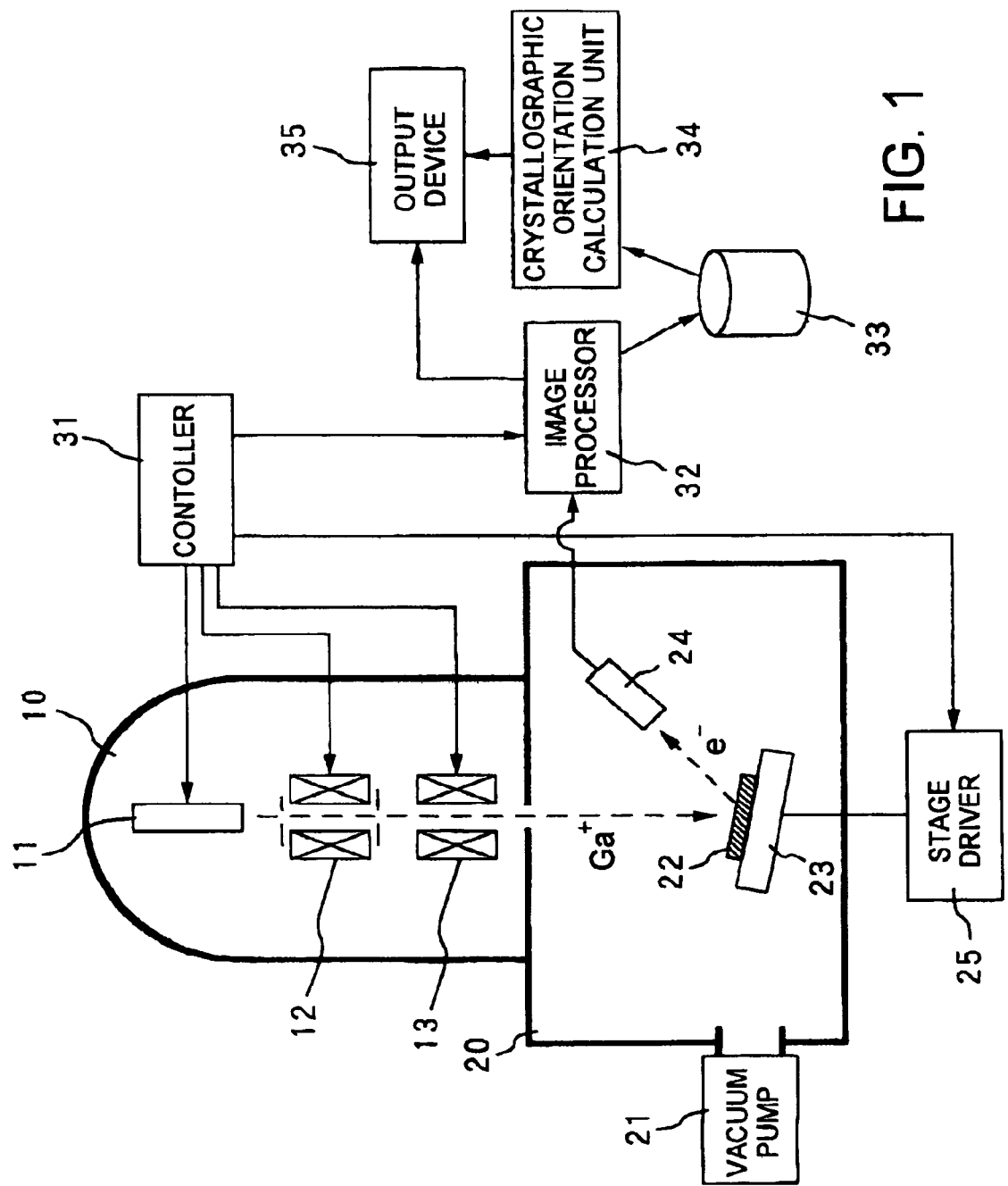
FIG. 1 is a block diagram illustrating the construction of the apparatus for crystal analysis according to an embodiment of the present invention.

The method of crystal analysis according to the present invention is intended for analyzing the crystallographic orientations and crystal systems of a specimen surface based on the relation between the intensity of the secondary electron emitted from the specimen when the specimen surface is irradiated with an ion beam and the angle of incidence of the ion beam impinging on the specimen. It is possible to obtain the data that represent a two-dimensional distribution of the crystallographic orientations of crystal grains on a specimen surface by performing an observation by means of the scanning ion microscope while varying the incidence angle of the ion beam with respect to a specimen surface and analyzing a plurality of the scanning ion microscope images (hereinafter referred to as the SIM images) acquired at different incidence angles. This data representative of the two-dimensional distribution is equivalent to an inversion pole figure obtained by the measurements according to the EBSP method. Thus, the apparatus for crystal analysis according to an embodiment of the present invention, shown in FIG. 1, represents a scanning ion microscope operated by a focused ion beam, attached with apparatuses required for identifying and analyzing the crystallographic orientations. Explanation is presented below regarding the apparatus for crystal analysis shown in FIG. 1.

The crystal analysis apparatus is provided with: ion optical system 10 and specimen chamber 20 that make up a scanning ion microscope; controller 31 that controls the entirety of the crystal analysis apparatus; image-processor 32 for acquiring SIM images; storage device 33 that stores SIM images for respective incidence angles; crystallographic orientation calculation unit 34 that calculates a two-dimensional distribution of the crystallographic orientations of the specimen surface based on a plurality of SIM images for different incidence angles; and output device 35 that displays or prints the SIM images and the calculated two-dimensional distribution.

Ion optical system 10 is provided with ion source 11 that generates an ion beam to be irradiated, condensing optical system 12 that accelerates and condenses the ion beam carried from ion source 11, and deflecting optical system 13 that scans the surface of specimen 22 with the focused ion beam in the in-plane directions (X, Y directions) of the surface of specimen 13 to perform observations by the scanning ion microscope Gallium ions (Ga$^+$) are typically used for the ion beam. Ion source 11, condensing optical system 12 and deflecting optical system 13 are controlled by controller 31.

In specimen chamber 20 provided in communication with ion optical system 10, there are provided vacuum pump 21 for evacuating ion optical system 10 and specimen chamber 20, stage 23 for mounting specimen 22, and detector 24 for detecting secondary electrons (e$^-$) emitted from specimen 22 when specimen is irradiated with the ion beam. Stage 23 has a translation mechanism to displace specimen 22 in X, Y directions and also is structured to allow inclining specimen 22 to vary the angle of incidence of the ion beam with respect to specimen 22. In the present invention, if it is intended to perform a stricter analysis, then it is preferred to vary the azimuth of incidence of the ion beam on specimen 22 as well. In order to allow not only inclining specimen 22 but also varying the azimuth of incidence, as described above, stage 23 is also provided with at least a uniaxial angle adjustment mechanism, preferably multiaxial angle adjustment mechanism. Stage driver 25 is provided near specimen chamber 20 to drive the translation mechanism and angle adjustment mechanism. Stage driver 25 is controlled by controller 31.

Image processor 32 is intended for acquiring the SIM image based on both the detection signal of the secondary electrons supplied from detector device 24 and the synchronization signal synchronized with the deflection of the focused ion beam in deflecting optical system 13 supplied from controller 31. Crystallographic orientation calculation unit 34 calculates a crystallographic orientation for each position or zone on the surface of a specimen on the basis of the variation in the density of the SIM image when the angle of incidence of the ion beam is varied at each position or zone. It is possible in the present embodiment to calculate crystal systems of crystal grains at respective positions or zones as well if different crystal phases are mixedly present in the specimen.

Explanation is next given regarding a crystal analysis through the use of the above-described crystal analysis apparatus.

Specimen 22 is first mounted on stage 23, the ion beam supplied from ion source 11 is focused by condensing optical system 12, the focused ion beam is deflected by deflecting optical system 13 to irradiate the surface of specimen 22 so as to scan two-dimensionally. The secondary electrons emitted from specimen 22 are detected by detector 24, which generates a detection signal corresponding to the amount of the secondary electrons. Image processor 32 acquires the SIM image based of this detection signal and the synchronization signal supplied from controller 31, supplies the SIM image to output device 35 and also stores the SIM image in storage device 33. Controller 31 controls stage driver 25 to keep the angle of incidence of the ion beam with respect to specimen 22 fixed while acquiring one SIM image, and to vary the angle of incidence of the ion beam with respect to specimen 22 bit by bit with each acquisition of the SIM image. This control operation on stage driver 25 allows image processor 32 to successively acquire SIM images for differing angles of incidence of the ion beam and all of the acquired SIM images are stored in storage device 33.

When a sequence of the SIM images has been acquired for a predetermined range of the angle of incidence and stored in storage device 33, crystallographic orientation calculation unit 34 next reads out the SIM images from storage device 33, calculates the distribution of the crystallographic orientations within an observation zone in the surface of specimen 22 on the basis of the variation in density of the SIM image depending on the variation of the angle of incidence of the ion beam, and delivers the calculated results to output device 35 as, for example, a distribution diagram. As a result, a result of analysis can be obtained similar to the inversion pole figure by means of the EBSP method.

Explanation below regards the results obtained through actual measurements according to the method of crystal analysis of the present invention.

In the measurements, copper formed by the plating process was employed as a specimen. A copper crystal belongs to the cubic system and has the face-centered cubic lattice structure. With each change in the angle of incidence of the ion beam with respect to the specimen, an SIM image of the specimen was acquired by the scanning ion microscope using the focused ion beam. Gallium ions were employed for the ion beam, and 30 kV of the acceleration voltage and 10 pA of the specimen current were applied.

Figure 2:
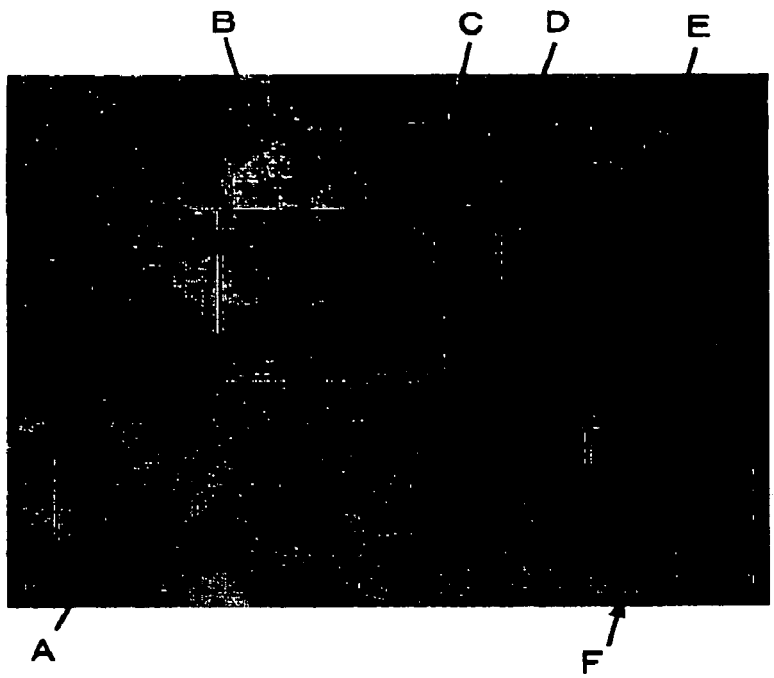
FIG. 2 is a scanning ion microscopic (SIM) photograph of a specimen.
Figure 3:
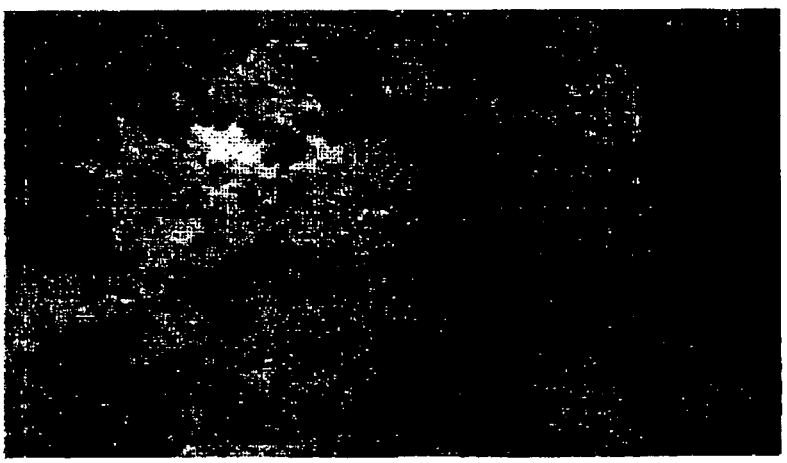
FIG. 3 is an inversion pole figure illustrating the processed result by the EBSP method for the crystallographic orientation of each of the crystal grains on the surface of the specimen shown in FIG. 2.
Figure 3:
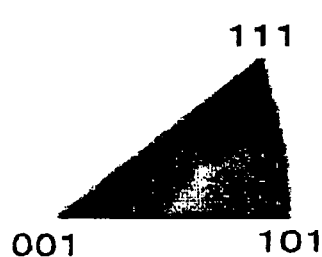

FIG. 2 represents an SIM image of a specimen when irradiating the specimen with an ion beam at an inclination angle of 0 degrees of the specimen, i.e., along the normal line of the specimen surface. The observation zones are set in this specimen as illustrated in A to F. FIG. 3 represents the inversion pole figure created for the same specimen by the EBSP method. While an inversion pole figure is commonly represented by a color picture, it is herein represented by a monochrome grayscale picture. The measurement conditions in the EBSP method are 20 kV of the acceleration voltage and 70 degrees of the inclination angle of the specimen.

Figure 4:
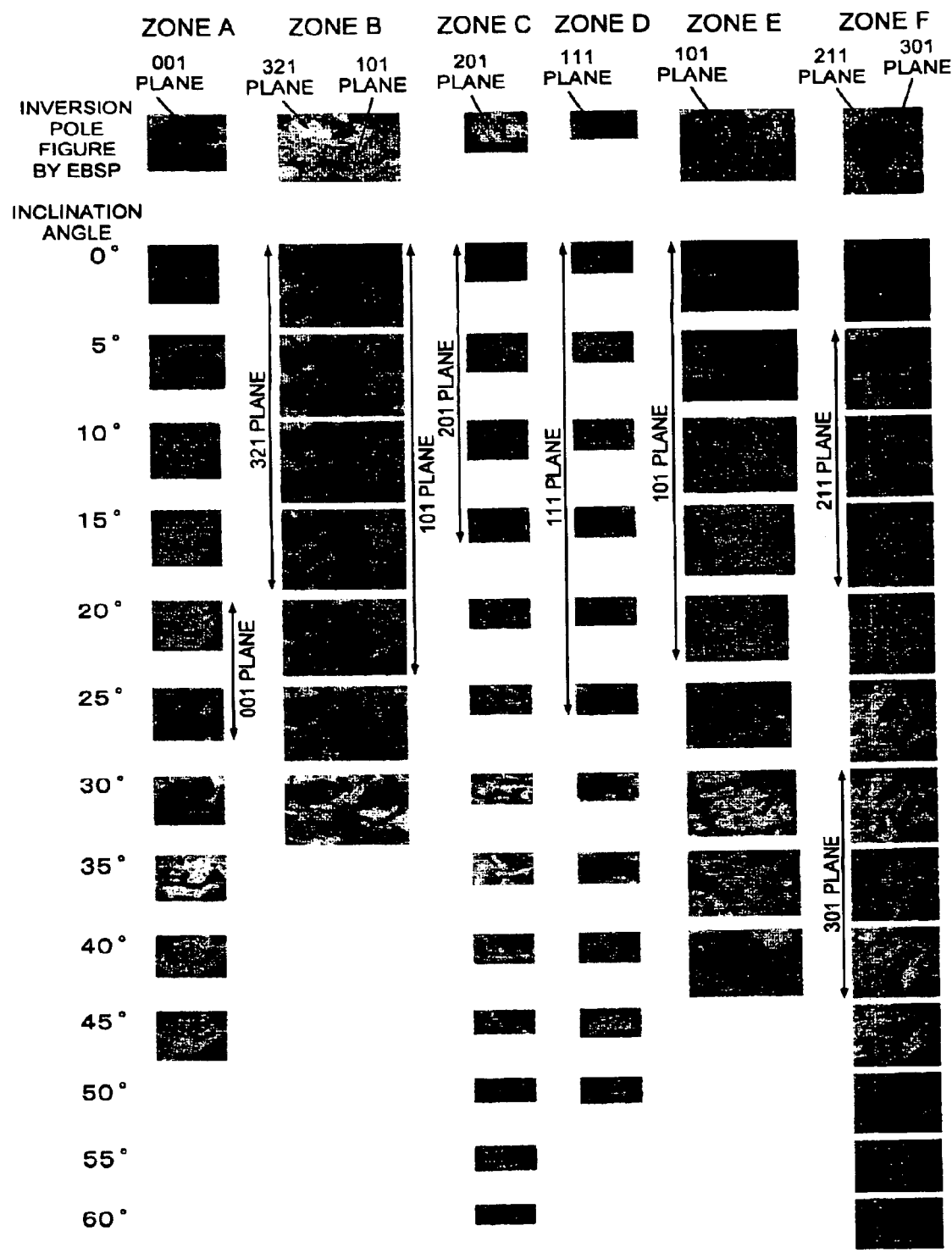
FIG. 4 is a diagram representing the correspondence of the inclination angles of the specimen in respective zones A to F shown in FIG. 2 to scanning ion microscopic images.

FIG. 4 represents the variation of the SIM images at intervals of 5 degrees of the inclination angle of the specimen in each of zones A to F shown in FIG. 2. The crystallographic orientation of each observation zone was identified in advance on the basis of the inversion pole figures shown in FIG. 3. Each of the images in the top row of FIG. 4 represents an inversion pole figure for each observation zone.

As known from FIG. 4, varying the inclination angle of the specimen yielded a definite change in the grayscale shade of the SIM image. A further analysis proved that there is a correlation between a half value of an angle of each crystallographic plane making with respect to 001 plane and the variation in the inclination angle that causes the contrast to vary from the maximum value of white to the maximum value of black, or from the maximum value of black to the maximum value of white. The angle variation that causes an SIM image to vary from the maximum value of white to the maximum value of black, or from the maximum value of black to the maximum value of white is referred to as a black-white inversion angle. Table 1 represents the black-white inversion angle measured for each crystal plane.

TABLE 1

| | Zone | | | | | | | |
|---|---|---|---|---|---|---|---|---|
| | A | B | | C | D | E | F | |
| Crystal plane | 001 | 321 | 101 | 201 | 111 | 101 | 211 | 301 |
| Angle (°) of each plane that makes with 001 plane of cubic system | 0 | 36.7 | 45 | 26.6 | 54.7 | 45 | 35.3 | 18.4 |
| Half value of angle that makes with 001 plane | 0 | 18.4 | 22.5 | 13.3 | 27.4 | 22.5 | 17.7 | 9.2 |
| Measured black-white inversion angle | 5 | 15 | 20 | 15 | 25 | 20 | 10 | 10 |

In addition, the ranges of angles corresponding to the measured black-white inversion angles are represented by two-headed arrows in FIG. 4. In this regard, only the 001 plane exhibited a different behavior, i.e., the grayscale shade of the image suddenly changes at a certain angle from white to black or from black to white, rather than gradually changes.

From the measured results described above, it is proven that the black-white inversion angle equals a half of an angle a crystal plane of interest makes with 001 plane and thus the crystallographic orientation in a desired position or zone in an SIM image can be discriminated by measuring the black-white inversion angle in the subject position or zone. Further, it is possible to identify the crystallographic orientation further strictly by taking into account an actual range of the inclination angle of the specimen corresponding to the black-white inversion angle, taking into account the pattern of the variation in the density or grayscale shade of the image, and changing the azimuth of incidence of the ion beam. Still further, it is also possible to determine the crystallographic orientation without measuring a black-white inversion angle by settling a plurality of angles of incidence used for the measurements in advance and simply comparing the densities or grayscale shades of the SIM images acquired at the respective settled angles.

As described above, the method of crystal analysis and the apparatus for crystal analysis according to the present invention allow the analysis and identification of the crystallographic orientations and crystal systems of fine crystal grains on the surface, thereby serving for the analysis of defectives and improvement in manufacturing management by, for example, applying to the measurements of the crystallographic orientations of a conductive layer and a semiconductor layer in the manufacture of a semiconductor device. Furthermore, the present invention offers advantages of improving the quality of products, obviating production of defectives and improving manufacturing processes, in the fields where the crystalline state and the crystallographic orientation of the material to be used affect the quality of the product.

While preferred embodiments of the present invention have been described using specific terms, such description is for illustrative purposes only, and it is to be understood that changes and variations may be made without departing from the spirit or scope of the following claims.

What is claimed is:

1. A method of analyzing a crystalline state on a surface of a specimen, comprising the steps of:
irradiating said specimen with an ion beam;
measuring secondary electrons generated by irradiation of said ion beam;
repeating said irradiating step and said measuring step with each variation in an angle of incidence of said ion beam with respect to said specimen; and
determining said crystalline state based on the variation in amount of said secondary electrons corresponding to the variation of said angle of incidence;
wherein said crystalline state is a crystallographic orientation of each of crystal grains, and said crystallographic orientation is determined based on a difference between the angle of incidence of said ion beam corresponding to maximum measured amount of said secondary electrons and the angle of incidence of said ion beam corresponding to minimum measured amount of said secondary electrons.

2. A method of analyzing a crystallographic orientation at a point or in a zone on a surface of a specimen, comprising the steps of:
irradiating said specimen while scanning with a focused ion beam;
measuring secondary electrons generated by irradiation of said ion beam to acquire a scanning ion microscopic image;
repeating said irradiating step and said measuring step with each variation in an angle of incidence of said ion beam with respect to said specimen; and
determining said crystallographic orientation based on the variation in densities of a plurality of said scanning ion microscopic images acquired at different angles of incidence;
wherein for said point or said zone on the surface, a difference between the angle of incidence corresponding to a darkest image of a plurality of said scanning ion microscopic images and the angle of incidence corresponding to a whitest image is calculated, and said crystallographic orientation at a point or in a zone is decided on a basis of said difference.

3. An apparatus for analyzing a crystallographic orientation at each point or in each zone on a surface of a specimen, comprising:
an ion optical system that irradiates the surface of the specimen in a specimen chamber while scanning with a focused ion beam;
a detector that detects secondary electrons generated by irradiation of said ion beam and provides a detection signal;
an image processor that acquires scanning ion microscopic images based on said detection signal;
an angle adjustment unit that varies an angle of said specimen with respect to said focused ion beam;
a storage device that stores the scanning ion microscopic images acquired by said image processor;
a controller that controls said angle adjustment unit to keep said angle of said specimen fixed while acquiring one scanning ion microscopic image and varies said angle of said specimen with each acquisition of said scanning ion microscopic image; and
a crystallographic orientation calculation unit that determines said crystallographic orientation based on a variation in densities of a plurality of said scanning ion microscopic images stored in said storage device;
wherein said crystallographic orientation calculation unit calculates, for said point or zone on the surface, a difference between the angle of incidence corresponding to a darkest image of a plurality of said scanning ion microscopic images and the angle of incidence corresponding to a whitest image, and decides said crystallographic orientation at a point or in a zone on a basis of said difference.

4. The apparatus according to claim 3, wherein said crystallographic orientation calculation unit provides an output of data indicating a distribution of said crystallographic orientations on the surface of said specimen.

* * * * *